United States Patent [19]

Graneto et al.

[11] Patent Number: 5,093,347
[45] Date of Patent: Mar. 3, 1992

[54] 3-DIFLUOROMETHYLPYRAZOLECARBOX-AMIDE FUNGICIDES, COMPOSITIONS AND USE

[75] Inventors: Matthew J. Graneto, St. Louis; Wendell G. Phillips, Glencoe, both of Mo.

[73] Assignee: Monsanto Company, St. Louis, Mo.

[21] Appl. No.: 725,151

[22] Filed: Jul. 3, 1991

Related U.S. Application Data

[63] Continuation-in-part of Ser. No. 646,899, Jan. 28, 1991, abandoned.

[51] Int. Cl.$^5$ .................. A01N 43/56; C07D 231/14
[52] U.S. Cl. ...................................... 514/406; 548/378
[58] Field of Search ......................... 548/378; 514/406

[56] References Cited

U.S. PATENT DOCUMENTS 4,742,074 5/1988 Nishida et al. ..................... 548/378

Primary Examiner—Robert W. Ramsuer
Attorney, Agent, or Firm—Grace L. Bonner; George R. Beck; Howard C. Stanley

[57] ABSTRACT

Novel 3-difluoromethyl-1-methyl-N-(substituted-indane-4-yl)pyrazole-4-carboxamides useful as fungicides, particularly effective in alleviating infections in diseased plants.

17 Claims, No Drawings

3-DIFLUOROMETHYLPYRAZOLECARBOXAMIDE FUNGICIDES, COMPOSITIONS AND USE

This application is a continuation-in-part of co-pending application Ser. No. 07/646,899, filed Jan. 28, 1991 abandoned.

FIELD OF THE INVENTION

The present invention provides novel 3-difluoromethyl-1-methyl-N-(substituted-indane-4-yl)pyrazole-4-carboxamides and their use as fungicides.

BACKGROUND OF THE INVENTION

Fungicides for control of agricultural diseases may be used for preventative applications, for example, as a seed treatment, or for curative applications, applied to growing plants already infected with a fungal disease. An efficacious curative fungicide may completely cure the disease, that is, rid the plant of the fungal infection, or it may alleviate the infection to such a degree that plant growth and/or crop yield are not unacceptably inhibited by the disease.

Other carboxamide fungicides are known in the art. U.S. Pat. No. 4,742,074, issued May 3, 1988, to Nishida et al., discloses various N-(substituted-indanyl)-pyrazole-4-carboxamides useful as fungicides for various agronomic diseases. Included is 1-methyl-3-trifluoromethyl-N-(1,1,3-trimethylindane-4-yl)pyrazole-4-carboxamide, described as useful against rice sheath blight (preventative and curative), brown rust of wheat (curative), and apple scab disease (preventative). However, there remains a need in the art for superior fungicides, particularly for curative applications for which a high level of systemic activity is highly advantageous.

It is therefore an object of this invention to provide compounds having a broad spectrum of activity against fungal diseases of plants. It is a further object of this invention to provide compounds having a high level of effectiveness in curing fungal diseases in affected plants. It is another object of this invention to provide compounds that readily move through a diseased plant after application to another part of the plant, e.g., its leaves, fruit, or stems. Further, it is an object of this invention to provide methods of preventing and, more importantly, curing fungal diseases of plants at comparatively lower application rates, resulting in lower residues in the plants and the environment.

SUMMARY OF THE INVENTION

Therefore, the present invention comprises the compounds having the structure

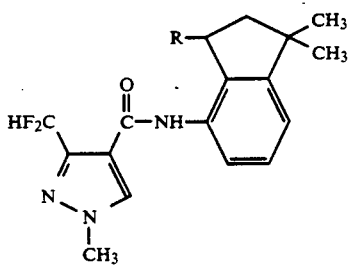

wherein R is hydrogen or methyl; compositions containing these compounds, and methods of using them to control agricultural fungal diseases, including curing or alleviating infections.

DETAILED DESCRIPTION OF THE INVENTION

The preferred compound of the present invention is 3-difluoromethyl-1-methyl-N-(1,1,3-trimethylindane-4-yl)pyrazole-4-carboxamide, which has the structure

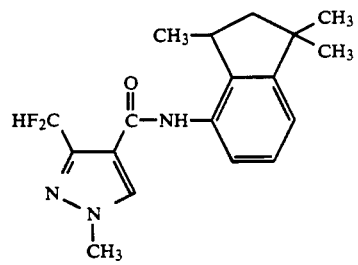

Related compounds, such as 3-difluoromethyl-N-(1,1,3-trimethylindane-4-yl)pyrazole-4-carboxamide and 3-difluoromethyl-1-ethyl-N-(1,1,3-trimethylindane-4-yl)pyrazole-4-carboxamide, as well as their 1,1-dimethylindane analogs, are also useful as fungicides.

The compounds of the present invention are prepared by reacting 3-difluoromethyl-1-methyl-4-pyrazole carbonyl chloride with the appropriate 4-aminoindane under amide-forming conditions. This pyrazole carbonyl chloride can be prepared by known methods using ethyl difluoroacetoacetate, triethyl-orthoformate, and methyl hydrazine to form the carboxylic ester, which is easily converted to the acid chloride.

Details of such a reaction are given in the following example. This example is illustrative only and not meant to be limiting in any way.

EXAMPLE 1

Synthesis of 3-difluoromethyl-1-methyl-N-(1,1,3-trimethylindane-4-yl)pyrazole-4-carboxamide.

Ethyl difluoroacetoacetate, 44.9 g (0.27 mole), obtained from Starks Chemicals, was mixed with triethylorthoformate, 54.3 mL (0.33 mole), and 80 mL acetic anhydride. The mixture was refluxed for 2 hours and then heated to approximately 140° C. to distill off volatiles. It was held at that temperature for 2 hours and allowed to cool. It was then distilled under reduced pressure to yield 47.8 g of a light yellow oil.

To this oil was added 200 mL of ethanol and the mixture held at 10°-15° C. while methyl hydrazine, 11.7 mL (0.22 mole), in ethanol, was added dropwise. After addition was complete, the mixture was refluxed for 1½ hours and allowed to cool. The mixture was concentrated under vacuum. Methylene chloride and 2 N HCl were added. The methylene chloride layer was separated and dried over magnesium sulfate. The solvent was removed under vacuum and the crude product recrystallized from toluene to yield a light yellow solid, 32.4 g. m.p. 25°-27° C. This was identified as ethyl 3-difluoromethyl-1-methyl-4-pyrazole carboxylate. This ester was treated with 64 mL of 2.5 N sodium hydroxide, and the resulting salt acidified to yield the acid, 24.5 g.

This pyrazole carboxylic acid was treated with oxalyl chloride, 15.2 mL (0.174 mole), in toluene, and a few drops of dimethylformamide was added. The mixture was concentrated under reduced pressure to yield the carboxyl chloride as a light amber oil, 26.9 g.

To this acid chloride, in 150 mL methylene chloride, at 0° C., was added dropwise a solution of 2,3-dedihydro-1,1,3-trimethyl-1H-inden-4-amine, 24.9 g (0.142 mole), and 19.8 mL (0.142 mole) triethylamine, dissolved in 50 mL methylene chloride. This mixture was stirred overnight at room temperature. It was then washed once with water and twice with 200 mL 2 N HCl and dried over magnesium sulfate. The solvent was removed under reduced pressure to yield a solid which was recrystallized from toluene and washed with hexane to yield 34.2 g of the title compound as a white solid. m.p. 131°-134° C.

The other compound of the present invention may be similarly prepared.

The compounds of the present invention may be used as is without adding any other components, but generally, they are formulated into emulsifiable concentrates, wettable powders, suspension formulations, granules, dusts, liquids and the like by mixing with a solid or liquid carrier, a surface active agent and other auxiliaries for formulation.

The content of a compound of the present invention contained as an active ingredient in these formulations is 0.1 to 99.9%, preferably 0.2 to 80% by weight, and more preferably 2 to 50% by weight. The concentration of the active compound in the spray solutions as they are applied to growing plants will be much less, from about 10 ppm up to about 1000 ppm.

The exact amount of active ingredient per hectare to be employed in the treatment or prevention of disease is dependent upon various factors, including the plant species and stage of development of plants and disease, the amount of rainfall, and the specific adjuvants employed. In foliar applications a dosage of from about 30 to about 2000 g/ha, preferably from about 60 to about 250 g/ha, is usually employed. In soil applications a dosage of from about 100 to about 2000 g/ha, preferably from about 250 to about 500 g/ha is usually employed. Lower or higher rates may be required in some instances. One skilled in the art can readily determine from this specification, including the following examples, the optimum rate to be applied in any particular case.

The solid carriers include for example fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide, and the like. The liquid carrier includes for example aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water and the like.

The surface active agents used for emulsification, dispersion, wetting, etc, include for example anionic surface active agents, such as salts of alkyl sulfate, alkyl or aryl sulfonates, dialkylsulfo-succinates, salts of polyoxyethylene alkyl aryl ether phosphoric acid esters, or naphthalenesulfonic acid/formalin condensates, etc, and nonionic surface active agents, such as polyoxyethylene alkyl ether, polyoxyethylene polyoxypropylene block copolymers, sorbitan fatty acid esters, or polyoxyethylene sorbitan fatty acid esters, etc. The auxiliaries for formulation include for example lignosulfonates, alginates, polyvinyl alcohol, gum arabic, and CMC (carboxymethyl cellulose).

The compounds of the present invention may also be combined with other fungicides, plant growth regulators, fertilizers, herbicides, and insecticides. Penetrating agents, to increase systemic activity may also be added to the compounds of the present invention.

Diseases for which the compounds of the present invention may be used include, but are not limited to, those caused by species of Rhizoctonia, Botrytis, Alternaria, Cercosporidium, Pseudocercosporella, Puccinia, and Venturia.

Crops on which the compounds may be used include, but are not limited to, cereals, for example, wheat and rice; fruits, for example, apples and grapes; vegetables, for example, tomatoes; oil-producing crops, for example, peanuts, soybeans, and oilseed rape; and turf. Application methods to be used in fungal control on plants include, but are not limited to, direct application to the body of the plant by spraying or direct application means; soil treatment prior to or at the time of planting, or at any time during the life of the plant; and application to the seed o seed pieces prior to or at the time of planting. The latter two means expose the rhizosphere of the plant to the treatment compound.

It has surprisingly been found that the compounds of the present invention have superior fungicidal properties, particularly for curative applications, and more particularly for foliar, fruit, or stem applications for curative needs. While not wishing to be bound by this theory, it is possible that the difluoromethyl substituent provides better uptake of the compound and better movement throughout the plant when applied by contact with the foliage, fruit, or stems of the diseased plant. When such an application is made by spraying, the contact will generally be made with substantially the whole body of the plant above the soil.

The advantage of improved curative properties is in the lower use rates that are required to treat diseased plants. This results in significantly lower residues of the fungicide in the plant and its foliage, seed, or fruit, and in the environment. An improved curative fungicide also provides the advantage of reducing or eliminating the need for preventative applications of fungicides which may also reduce the level of pesticide residues in crops and the environment.

The compound prepared as in Example 1, hereinafter designated Compound A, has been tested for fungicidal effectiveness in a variety of tests, including both preventative and curative application methods. It has been compared to the compound of U.S. Pat. No. 4,742,074, mentioned above, believed to be the closest compound of the prior art. This known fungicide, hereinafter designated Compound B, was prepared according to Synthesis Example 8 (Compound 19) of that patent, the full text of which is incorporated herein by reference. The following examples describe the tests conducted and the results thereof. As demonstrated in Examples 2 through 7, Compound A of the present invention is superior to the prior art compound in curative applications to the plant foliage, fruit, or stems.

EXAMPLE 2

Test for curative activity against apple scab.

Young apple plants (cultivar: McIntosh) are inoculated with *Venturia inaequalis*, 100E6 spore/mL, and placed in a mist chamber at 20° C. At 24, 48, or 72 hours after inoculation, four plants for each treatment level are sprayed with 12 mL of an acetone/water formulation of 20, 100, or 500 ppm of the test compound(s). Each plant is evaluated at 17 and 24 days post-infection for the level of disease severity.

The results of the average percent disease for the four plants per treatment level are reported in Table 1, at 17 days post-infection, and Table 2 at 24 days. Compound A was much more effective at 100 ppm than Compound B at 500 ppm and approximately as effective at 20 ppm as Compound B at 500 ppm.

TABLE 1

| TREATMENT COMPOUND | RATE (ppm) | PERCENT DISEASE SEVERITY | | |
|---|---|---|---|---|
| | | 24 HR | 48 HR | 72 HR |
| A | 500 | 0.0 | 2.0 | 2.0 |
| | 100 | 0.0 | 6.0 | 1.0 |
| | 20 | 3.0 | 4.0 | 8.0 |
| B | 500 | 4.0 | 6.0 | 26.0 |
| | 100 | 6.0 | 14.0 | 44.0 |
| | 20 | 3.0 | 22.0 | 33.0 |
| Control | — | 50.0 | 88.6 | 81.5 |

TABLE 2

| TREATMENT COMPOUND | RATE (ppm) | PERCENT DISEASE SEVERITY | | |
|---|---|---|---|---|
| | | 24 HR | 48 HR | 72 HR |
| A | 500 | 1.0 | 2.0 | 9.0 |
| | 100 | 4.0 | 4.9 | 9.1 |
| | 20 | 10.2 | 34.3 | 61.9 |
| B | 500 | 68.1 | 43.8 | 34.3 |
| | 100 | 83.8 | 61.0 | 34.3 |
| | 20 | 36.6 | 65.8 | 87.4 |
| Control | — | 90.5 | 94.0 | 87.4 |

EXAMPLE 3

Test for curative activity against tomato early blight.

Seedling tomato plants (cultivar: Rutgers) in 3" pots are inoculated with *Alternaria solani*, 5E4 spores/mL, and maintained in a mist chamber. At 24 hours after inoculation, five plants per treatment level are sprayed with 10 mL of solution containing 1000, 500, 100, and 20 ppm of the test compounds. At 5 days post-inoculation each plant is evaluated for the level of disease, and the percent control, compared to an inoculated, untreated control, is calculated.

The results of this test are shown in Table 3. Compound A is clearly superior to Compound B, with 20 ppm of Compound A demonstrating more curative activity than 1000 ppm of Compound B.

TABLE 3

| TREATMENT COMPOUND | RATE (ppm) | PERCENT CONTROL |
|---|---|---|
| A | 1000 | 90 |
| | 500 | 90 |
| | 100 | 92 |
| | 20 | 73 |
| B | 1000 | 54 |
| | 500 | 42 |
| | 100 | 62 |
| | 20 | 57 |
| Control | — | 0 |

EXAMPLE 4

Test for curative activity against vine grey mold.

Grape berries are placed one per well in 12-well plates and each inoculated with *Botrytis cinerea*, 1 mL of 10E6 spores/mL. After 24 hours the incubation is temporarily interrupted for treatment with 1 mL of an acetone/water formulation of 1000, 500, or 200 ppm of the test compounds. The plates are kept in a dark incubator at 20° .C for seven days and the severity of the disease evaluated by the following scale:

0 = No disease
1 = Mild disease
2 = Moderate disease
3 = Severe disease

The results of this test, reported as the average of five berries per treatment level are shown in Table 4. Compound A was as effective at 200 ppm as Compound B at 1000 ppm.

TABLE 4

| TREATMENT COMPOUND | RATE (ppm) | DISEASE RATING |
|---|---|---|
| A | 1000 | 0.5 |
| | 500 | 1.4 |
| | 200 | 2.0 |
| B | 1000 | 1.9 |
| | 500 | 2.2 |
| | 200 | 2.4 |
| Control | — | 3.0 |

EXAMPLE 5

Test for curative activity against wheat leaf rust.

Young wheat plants (cultivar: Hart) are grown in 3" pots and inoculated at the two leaf stage with *Puccinia recondita*, 2 mL of 5E4 spores/mL. 48 hours later each plant is sprayed with 2 mL of an acetone/water/Tween ®20 formulation containing 100, 20, 5, or 1 ppm of the test compounds. After 10 days in the growth chamber at 21° C., each plant is evaluated for disease level and the percent disease control compared to an inoculated, untreated control is calculated.

The results of this test, reported as the average of five replicates, are shown in Table 5. The differences between the two test compounds were statistically significant at 5 ppm, Compound A being superior.

TABLE 5

| TREATMENT COMPOUND | RATE (ppm) | PERCENT CONTROL |
|---|---|---|
| A | 100 | 100 |
| | 20 | 100 |
| | 5 | 99.9 |
| | 1 | 69.3 |
| B | 100 | 100 |
| | 20 | 100 |
| | 5 | 95.5 |
| | 1 | 58.8 |
| Control | — | 0 |

EXAMPLE 6

Test for curative activity against wheat true eyespot.

Mature wheat plants (cultivar: Slepjner) in 2.25" pots are inoculated with Pseudocercosporella herpotrichoides, 2 mL of 3E6 spores/mL. Five days later nine plants per treatment level are sprayed with an acetone/water/Tween ®20 formulation containing 1000, 500, or 250 ppm of the test compounds. After 5 weeks in the growth chamber each plant is evaluated for disease and the percent disease control compared to an inoculated, untreated control is calculated.

The results of this test are shown in Table 6. Compound A was as effective at 250 ppm as Compound B was at 1000 ppm.

TABLE 6

| TREATMENT COMPOUND | RATE (ppm) | PERCENT CONTROL |
| --- | --- | --- |
| A | 1000 | 96 |
|   | 500 | 83 |
|   | 250 | 83 |
| B | 1000 | 83 |
|   | 500 | 77 |
|   | 250 | 63 |
| Control | — | 0 |

EXAMPLE 7

Test for curative activity against Alternaria leaf spot of oil seed rape.

Oilseed rape seedlings (cultivar: Bienvenu) are grown in 7 cm pots and at the first leaf stage are inoculated with *Alternaria brassicae Alternaria*, 2 mL of 2E4 spores/mL per pot. After 24 hours, nine plants per treatment level are sprayed with an acetone/water/Tween®20 formulation containing 1000, 500, or 300 ppm of the test compounds. After 7 days, each plant is evaluated for disease severity and the percent disease control compared to an inoculated, untreated control is calculated.

The results of three repetitions of this test are shown in Tables 7A, B, and C. Compound A was superior to Compound B in all tests, exhibiting a two- to three-fold increase in effectiveness.

TABLE 7A

| TREATMENT COMPOUND | RATE (ppm) | PERCENT CONTROL |
| --- | --- | --- |
| A | 1000 | 90 |
|   | 500 | 77 |
|   | 300 | 100 |
| B | 1000 | 77 |
|   | 500 | 57 |
|   | 300 | 67 |
| Control | — | 0 |

TABLE 7B

| TREATMENT COMPOUND | RATE (ppm) | PERCENT CONTROL |
| --- | --- | --- |
| A | 500 | 100 |
|   | 300 | 72 |
| B | 500 | 72 |
|   | 300 | 33 |
| Control | — | 0 |

TABLE 7C

| TREATMENT COMPOUND | RATE (ppm) | PERCENT CONTROL |
| --- | --- | --- |
| A | 1000 | 77 |
|   | 500 | 66 |
|   | 250 | 43 |
| B | 1000 | 43 |
|   | 500 | 57 |
|   | 250 | 23 |
| Control | — | 0 |

EXAMPLE 8

Test against oilseed rape dark leafspot in vitro.

Inhibition of Alternaria brassicae is measured in vitro for each of the test compounds. Each compound is incorporated in potato dextrose agar at 10, 1, or 0.1 ppm. Each plate is inoculated and the radial growth of the fungus is measured after seven to ten days. The average growth for two plates per treatment level is obtained and the percent control compared an untreated plate calculated.

The results of this test are shown in Table 8. Compound A provided superior fungal inhibition.

TABLE 8

| TREATMENT COMPOUND | RATE (ppm) | PERCENT CONTROL |
| --- | --- | --- |
| A | 10 | 100 |
|   | 1 | 68 |
|   | 0.1 | 41 |
| B | 10 | 71 |
|   | 1 | 58 |
|   | 0.1 | 28 |
| Control | — | 0 |

EXAMPLE 9

Test for preventative activity against oilseed rape dark leafspot.

The method of Example 7 was followed except that the plants are sprayed with the test compounds one day prior to inoculation. Disease control is evaluated seven days post-infection. The results of this test are shown in Table 9. Compound A was more effective at 500 ppm than Compound B was at 1000 ppm.

TABLE 9

| TREATMENT COMPOUND | RATE (ppm) | PERCENT CONTROL |
| --- | --- | --- |
| A | 1000 | 84 |
|   | 500 | 78 |
|   | 250 | 56 |
| B | 1000 | 69 |
|   | 500 | 50 |
|   | 250 | 29 |
| Control | — | 0 |

EXAMPLE 10

Test for preventative activity against vine grey mold.

The method of Example 4 is followed except that the compounds are applied at the given treatment levels prior to inoculation. Disease severity is evaluated at 7 days post-infection.

The results of two repetitions of this test are shown in Tables 10A and 10B. They are reported as the average of five berries per treatment level. Compound A demonstrated a two-to five-fold improvement in activity over Compound B. The results of a third test, wherein the berries are coated with the test compound mixed with agarose and only four replicates per treatment level are used, are reported in Table 10C. Compound A was more effective at 125 ppm as Compound B was at 500 ppm.

TABLE 10A

| TREATMENT COMPOUND | RATE (ppm) | DISEASE RATING |
| --- | --- | --- |
| A | 1000 | 0.4 |
|   | 500 | 0.7 |
|   | 200 | 0.9 |
| B | 1000 | 0.7 |
|   | 500 | 1.0 |
|   | 200 | 1.2 |
| Control | — | 3.0 |

TABLE 10B

| TREATMENT COMPOUND | RATE (ppm) | DISEASE RATING |
|---|---|---|
| A | 1000 | 0 |
|  | 500 | 0.1 |
|  | 200 | 0.5 |
| B | 1000 | 1.0 |
|  | 500 | 1.6 |
|  | 200 | 2.3 |
| Control | — | 2.5 |

TABLE 10C

| TREATMENT COMPOUND | RATE (ppm) | DISEASE RATING |
|---|---|---|
| A | 500 | 0.8 |
|  | 250 | 1.8 |
|  | 125 | 1.8 |
| B | 500 | 3.0 |
|  | 250 | 2.8 |
|  | 125 | 3.0 |
| Control | — | 3.0 |

EXAMPLE 11

Test for preventative activity against peanut white mold.

Peanut plants, 12 to 14 days old, are grown in 7.65 cm$^2$ pots. Each plant, including the soil surface, is sprayed with 2 mL of a water/acetone/Tween ®20 formulation containing 500, 100, 20, 5, or 1 ppm of the test compounds. The next day two grams of a 21-day, dried, oat seed culture of *Sclerotium rolfsii* is spread on the surface of the soil in each pot. After 10 days in the growth chamber, each plant is evaluated for the level of disease by the following scale and the average of five plants per treatment level is calculated.

1 = No disease
2 = Slight disease, slight mycelium, no lesion
3 = Moderate disease, mycelium and small lesion
4 = Moderate/heavy disease, mycelium and lesion
5 = Heavy disease, plan The results of this test are given in Table 11. Compound A exhibited a two- to five-fold superiority over Compound B.

TABLE 11

| TREATMENT COMPOUND | RATE (ppm) | DISEASE RATING |
|---|---|---|
| A | 500 | 1.0 |
|  | 100 | 1.2 |
|  | 20 | 1.4 |
|  | 5 | 2.4 |
|  | 1 | 2.8 |
| B | 500 | 1.0 |
|  | 100 | 1.4 |
|  | 20 | 2.6 |
|  | 5 | 3.2 |
|  | 1 | 4.0 |
| Control | — | 4.6 |

EXAMPLE 12

Field test in peanuts.

Peanut plants are grown in plots 6 feet long by one row. Each treatment level is applied to four replicate plots. At 30 days after planting, test compounds are applied to the plants by spraying four times at 14-day intervals at rates equivalent to 16, 8, 4, or 2 ounces of active ingredient per acre. For some plots the test compound is mixed with Penetrator 3 ®, a surfactant known to enhance activity of systemic fungicides, at 0.125% v/v. Disease, consisting primarily of late leafspot, *Cercosporidium personatum*, is allowed to develop naturally and evaluated regularly and just prior to harvest. The results of the last evaluation, reported as the average disease severity of the four plots per treatment level, are shown in Table 12. Compound A is superior to Compound B and the activity of Compound A is enhanced by the penetrating agent.

TABLE 12

| TREATMENT COMPOUND | RATE (oz/A) | DISEASE RATING |
|---|---|---|
| A | 16 | 2.4 |
|  | 8 | 6.1 |
|  | 4 | 6.9 |
|  | 2 | 9.6 |
| A + Penetrator 3 | 8 | 2.7 |
|  | 4 | 5.5 |
|  | 2 | 11.1 |
| B | 16 | 8.8 |
|  | 8 | 9.2 |
|  | 4 | 13.1 |
|  | 2 | 18.8 |
| B + Penetrator 3 | 8 | 8.9 |
|  | 4 | 11.9 |
|  | 2 | 17.5 |
| Control | — | 35.6 |

EXAMPLE 13

Test for preventative activity against rice sheath blight.

Rice plants, 11 to 15 days old, are gown in 7.65 cm$^2$ pots. Each plant in the treatment groups is treated by spraying both the foliage and the soil surface, each with 2 mL of a water/acetone/Tween ®20 formulation containing 0.5, 0.1, or 0.02 mg/mL of Compound A. The pots are placed in flood trays which are filled with water to the soil line. Two days later approximately two grams of Rhizoctonia solani, grown on a rice grain inoculum for four to eight weeks, is applied to the base of the rice plants in each pot. After 7 days in the growth chamber, each plant is evaluated for the level of disease control as compared to untreated controls by the following scale and the average of five plants per treatment level is calculated.

0 = No activity
1 = Low activity
2 = Moderate activity
3 = High activity

The results of this test are given in Table 13.

TABLE 13

| Concentration mg/mL | Activity Rating |
|---|---|
| 0.5 | 3 |
| 0.1 | 3 |
| 0.02 | 3 |

We claim:

1. A compound of the formula

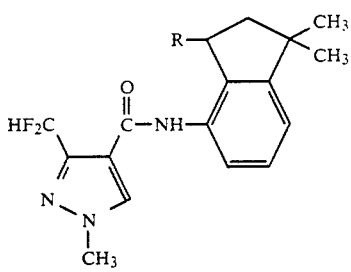

wherein R is hydrogen or methyl.

2. 3-Difluoromethyl-1-methyl-N-(1,1,3-trimethylindane-4-yl)pyrazole-4-carboxamide.

3. Fungicidal compositions comprising a compound of claim 1 and an agronomically acceptable carrier.

4. The fungicidal composition of claim 3 wherein the compound is 3-difluoromethyl-1-methyl-N-(1,1,3-trimethylindane-4-yl)pyrazole-4-carboxamide.

5. A method of controlling fungal disease of a plant comprising applying a compound of claim 1 to the plant locus.

6. The method of claim 5 wherein said compound is 3-difluoromethyl-1-methyl-N-(1,1,3-trimethylindane-4-yl)pyrazole-4-carboxamide.

7. The method of claim 6 wherein said plant locus is the seed of said plant.

8. The method of claim 6 wherein said plant locus is the foliage of said plant.

9. The method of claim 6 wherein said plant locus is the rhizosphere of said plant.

10. A method of alleviating fungal disease of a plant comprising applying a compound of claim 1 to the locus of a diseased plant.

11. The method of claim 10 wherein said compound is 3-difluoromethyl-1-methyl-N-(1,1,3-trimethylindane-4-yl)pyrazole-4-carboxamide.

12. The method of claim 11 wherein said fungal disease is caused by a species of Botrytis, Alternaria, or Venturia.

13. The method of claim 12 wherein said fungal disease is caused by Botrytis cinerea and said diseased plant is grape vine.

14. The method of claim 11 wherein the locus of said plant is the foliage.

15. The method of claim 11 wherein the locus of said plant is the fruit.

16. The method of claim 11 wherein the locus of said plant is the stem.

17. The method of claim 11 wherein the locus of said plant is substantially the whole plant above the soil.

* * * * *